US006797705B2

(12) United States Patent  (10) Patent No.: US 6,797,705 B2
Daniels  (45) Date of Patent: Sep. 28, 2004

(54) RHAMNAN SULPHATE COMPOSITION FOR TREATMENT OF ENDOTHELIAL DYSFUNCTION

(75) Inventor: Bruce Alan Daniels, Oklahoma City, OK (US)

(73) Assignee: EndoMatrix, Inc., Santa Rosa, CA (US)

( * ) Notice: Subject to any disclaimer, the term of this patent is extended or adjusted under 35 U.S.C. 154(b) by 0 days.

(21) Appl. No.: 10/320,309

(22) Filed: Dec. 16, 2002

(65) Prior Publication Data

US 2004/0116377 A1 Jun. 17, 2004

(51) Int. Cl.[7] ..................... A61K 31/715; A61K 31/727

(52) U.S. Cl. ............................. 514/54; 514/53; 514/56

(58) Field of Search ............................... 514/54, 53, 56

(56) References Cited

U.S. PATENT DOCUMENTS

| | | |
|---|---|---|
| 4,758,283 A | 7/1988 | Takemura |
| 5,268,366 A | 12/1993 | Maeda |
| 5,321,133 A | 6/1994 | Colliec |
| 5,698,534 A | 12/1997 | Nagaoka |
| 5,948,405 A | 9/1999 | Cedro |

FOREIGN PATENT DOCUMENTS

JP        411080003 A  *  3/1999

OTHER PUBLICATIONS

Tanner, Felix C., "Oxidized Low Density Lipoproteins inhibit Relaxations of Porcine Coronary Arteries" Circulation vol. 83 No. 6 Jun. 1991 pp. 2012–2020.
Hiraoka, Atsushi. "Capillary–Isotachophoretic Analyses of Algal Acidic Polysaccharides . . . " Chem Pharm Bull Mar. 1992. vol. 40, No. 3, pp. 783–785.
Hayakawa, Yumiko.et al. "Inhibition of Thrombin by Sulfated polysaccharides isolated from Green Algae" Biochim Biophys Acta 1543 (2000) pp. 86–94.
Petrie, Jr, et al. "Endothelial Nitric Oxide production and Insulin Sensitivity." Circulation.Apr. 1, 1996. vol. 93, No. 7. pp. 1331–1333.
Van Den Born, J etal. "Vessel Wall heparan sulfate and transcapillary passage of albumin in experimental diabetes in the rat." Nephrol Dial Transplant 1997, vol. 12 supp. 2, pp. 27–31.
Dubois–Rande, Jean Luc, et al. L–Arginine Improves endothelium–dependent Relaxation of Conductance and Resistance Coronary Arteries in Coronary Artery Disease J of Cardiov Pharmac 1992, vol. 20, Supp 12. pp. S211–S213.
Luscher, TF, et al. "The Endothelial L–Arginine/Nitric Oxide Pathway and Renal Circulation" Klin Wochenschr 1991, vol. 69, pp. 603–609.
Bassenge, E, "Clinical relevance of endothelium–derived Relaxing Factor" Br. J. Clin Pharmac 1992, vol. 34 pp. 37S–42S.
Hishikawa, Keiichi,.et al. "L–Arginine as an Antihypertensive Agent" J. of Cardiovascular Pharmac vol. 20, Supp 12 pp. S196–S197.

(List continued on next page.)

Primary Examiner—James O. Wilson
Assistant Examiner—Everett White
(74) Attorney, Agent, or Firm—Ali Kamarei

(57) ABSTRACT

The invention described is a method and composition for inducing cell surface anti-thrombotic activity in endothelial cells comprising administering to a patient a therapeutically-effective amount of Rhamnan Sulphate. The dose of Rhamnan Sulphate is equivalent to between approximately 8,000 IU and 12,000 IU of heparin activity daily on variable schedule or optionally at single dosage of 7.5 mg/kg, that is repeated on a daily basis as needed, to lower the incidence of thrombus formation or to lower the incidence of hard clot formation.

25 Claims, 3 Drawing Sheets

Hard Clot
Soft Clot

OTHER PUBLICATIONS

Raats, CJ, et al. "Glomerular heparan sulfate alterations: mechanisms and relevance for proteinuria" *Kidney Int* Feb. 2000, vol. 57, No. 2. pp. 385–400.

Harada, Naoki, et al. "Chemical Structure of Antithromoin–active Rhamnan Sulfate from Monostrom nitidum" *Biosci Biotech, Biochem* vol. 62, No. 9 pp. 1647–1658 1998.

Deux. JF, et al. "Low Molecular weight fucoidan prevents neointimal hyperplasia in rabbit iliac artery in–stent restenosis model," *Arterioscler Thromb Vasc Biol* Oct. 1, 2002.

Trento, Fabio, et al. "Antithrombin Activity of an Algal Polysaccharide" *Thrombosis Research* vol. 102, 2001 pp. 457–465.

* cited by examiner

Rham = Rhamnose residue

S = Sulfate Ester

RHAMNAN SULPHATE COMPOSITION FOR TREATMENT OF ENDOTHELIAL DYSFUNCTION

FIELD

This invention relates to a pharmacological composition and method that provides for surface anti-thrombotic activity of endothelial cells and without exerting any appreciable amount of blood anticoagulation. This composition is preferably used for patients susceptible to or suffering from a cardiovascular disorder or disease, and more particularly, but not by way of limitation, to a formulation with enhanced absorption characteristics for preventing and treating atherosclerosis, arteriosclerosis, congestive heart failure, arterial stenosis, cardiac cell hypertrophy, thrombogenicity, myocardial infarction, cerebrovascular ischemia, peripheral vascular ischemia, angina pectoris, hypertension or endothelial dysfunction, without appreciably increasing the patient's risk of hemorrhaging, either internal or as a result of an external injury.

BACKGROUND

Cardiovascular disorders and diseases resulting from cell surface thrombosis, and their associated complications are a principal cause of disabilities and deaths of individuals in the world. For example, in recent years more than 500,000 deaths have occurred annually in the United States alone as a result of coronary artery disease, and an additional 1,200,000 patients have been hospitalized for myocardial ischemia and infarction.

There has been significant and extensive research for effective long term treatment for disorders and diseases of the heart and arteries, such as atherosclerosis, arteriosclerosis, congestive heart failure, angina pectoris, and other diseases associated with the cardiovascular system. However, present treatments for such disorders are short term treatments such as administration of vasodilators, angioplasty, and by pass surgery. These treatments have serious shortcomings in long term effectiveness, thus they have met with general disapproval due to the risks associated with them. The use of vasodilator drugs and mechanical treatments for acute and chronic occlusive vascular diseases of the heart central and peripheral vascular systems have to date been ineffective for favorable long-term results and do not treat the underlying molecular processes causal for the diseases.

The focus of current treatment methods is to react to potentially immediate danger to one's life. Even the prescription of "statin" drugs such as Lovastatin, were originally designed to treat patients with significant risk of present danger of heart attacks due to high cholesterol levels. The only reason the long term risks associated with taking cholesterol reducing agents or "statins" was justified because of the immediate danger the high cholesterol levels presented to a patient. Almost all of the current treatment methods focus on reducing and/or eliminating the occlusion of larger arteries and none take into consideration that, for example, over 75% of fatal heart attacks are in patients with no present signs of significantly occluded arteries. The insertion of stents and such mechanical devices into larger arteries to prevent occlusion are only temporary procedures. Thus, the result is that myocardial infarction is temporarily delayed. However, such procedures merely postpone eventual myocardial infarction as the underlying molecular processes continue untreated. The result of the current treatments has had minimal impact on the long-term processes of atherosclerosis. For example a significant number of patients who receive angioplasty have a repeat coronary event within three to five years. The cost associated with these treatments, both in terms of medical expenses as well as fatalities and lost productivity, is enormous.

Furthermore, the rationale for using statin drugs to lower plasma cholesterol fails to explain why coronary heart attacks generally occur in individuals with non-critical blockages and why blockages do not occur in capillaries or veins. When used, statin drugs reduce the risk of a recurrent coronary event, only by 30 to 40%.

The rationale for vasoactive drugs is to reduce blood pressure by acting directly or indirectly on vascular and/or cardiac smooth muscle, thereby decreasing vascular resistance to flow. Such drugs do not treat initial cause of elevated pressure and abnormal flow. Rather, they seek to reduce the resulting effect of the disorder. Such drugs activate the sympathetic nervous system by way of a baroreceptor reflex to produce an increased heart rate and force of myocardial contraction, which are not beneficial or desirable effects. Other side effects for such drugs include headache, heart palpitations, anxiety, mild depression, myocardial infarction, congestive heart failure, fatigue and weakness. Further, pharmacological effect is not specific in its effect on the initial molecular cause of the disease activity, and treats a limited spectrum of effects in the diseases, which are dependent on several factors.

None of these treatment methods is directed towards the underlying disease processes, the molecular causes of the disease or disorders, or towards restoring the structure and function of the blood vessels to levels that reduce or eliminate the danger posed by cardiovascular diseases. There is no treatment to reduce the level of obstruction in arteries that are not severely occluded or to enhance the arteries inherent ability to resist thrombus formation, leaving these patients still at significant risk of a heart attack.

In view of the foregoing, there is a significant need for a pharmacological composition and method that is directed towards treating the underlying cardiovascular disease process, and towards restoring the structure and improving the functions of the blood vessel cells and in particular the function-structure properties of the endothelium which lines all blood vessels and the heart.

It is an objective of the present invention to provide a treatment, which is directed to preventing and minimizing dysfunctional atomic and molecular interactions within the human cellular matrix or cellular environment, which lead to cardiovascular disease and atherosclerosis.

It is another objective of the present invention to provide a treatment that is directed to retarding adverse consequences of free radicals generated in human cellular matrix. It is also another objective of the present invention to stimulate an increased production of nitric oxide within human cellular matrix or cellular environment.

It is yet another objective of the present invention treatment of cardiovascular diseases, in particular cell surface based thrombosis, without appreciably increasing blood anticoagulation activity in patients.

SUMMARY

The present invention provides for a method and composition for treatment of the mammalian cellular environment for the prevention of endothelial dysfunction comprising the step of administering to a patient a therapeutically-effective amount of Rhamnan Sulphate, or its physiologically acceptable salts, in therapeutic proportions.

The dose of Rhamnan Sulphate administered to the patient is equivalent to between approximately 2,000 IU and 200,000 IU of heparin activity daily. Alternatively, the dose of Rhamnan Sulphate is approximately 7.5 mg/kg as a single dose or repeated daily, or optionally substituted for by its functional analogs, in predetermined amounts to achieve the desired effects. A physiological acceptable salt of Rhamnan Sulphate is formed by covalently bonding L-Arginine to the Rhamnan Sulphate.

The invention also describes a method for inducing cell surface anti-thrombotic activity in endothelial cells for treatment of cardiovascular disease without appreciably increasing the risk of hemorrhaging in patients, comprising the step of oral administration to a patient a therapeutically-effective amount of Rhamnan Sulphate. The present invention uses a therapeutically-effective amount of Rhamnan Sulphate or their respective physiologically-acceptable salts or functional analogs, to provide a patient with protection against endothelial dysfunction, without appreciably increasing the patient's risk of internal or external hemorrhaging.

An advantage of the method and composition of the invention is that it possesses extremely potent antithrombotic activity and other inhibitory effects on cell surface coagulation assembly and activity for thrombus inhibition.

Another advantage of the described composition is that there is less peptide residual in extracting the composition from plant cells as compared to heparin from animal cells. Hence, it is less allergic reaction prone and has fewer immunogenic properties.

Yet another advantage is that since Rhamnan Sulphate is from plant cells, it has no potential for the transmission of potentially lethal and serious prion diseases such as mad cow disease.

Another advantage is that Rhamnan Sulphate has no potential for activating Platelet Factor IV and resulting in immune complex destruction of platelets as seen with heparin administration.

Finally, another advantage of Rhamnan Sulphate is that it is a functional substitute for heparin in applications requiring systemic anticoagulant activity such as dialysis, bypass surgery, and polymer tube coatings and devices for use in mammals and humans.

DETAILED DESCRIPTION

Figure 1:
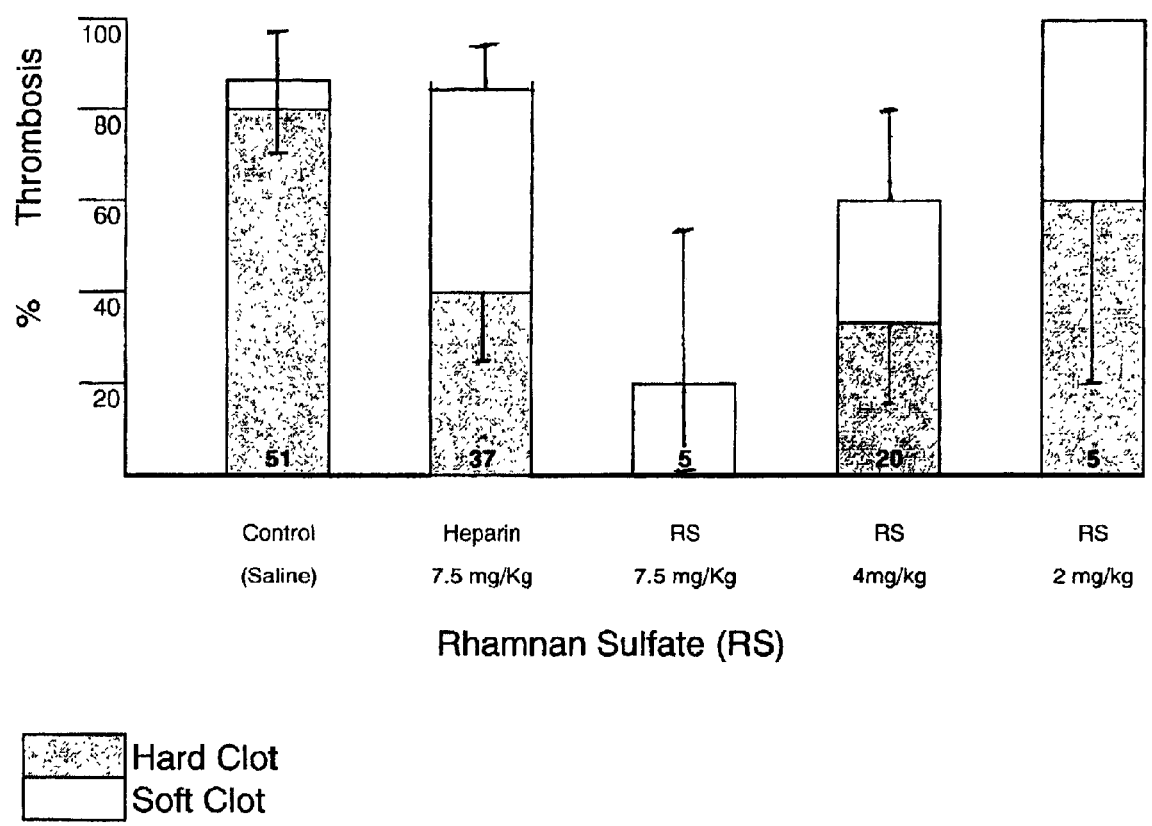
FIG. 1 is a graph comparing a control group to Heparin and groups of Rhamnan Sulphate at different dosages.

As has been previously described by the inventor, medical literature and thinking is pervasive with the thinking that high cholesterol levels cause occlusion of the coronary and other arteries, which then cause infarction and ischemia. The inventor, in U.S. Pat. Nos. 6,255,296 and 6,495,530, outlines the fact that endothelial cell surface thrombosis, rather than cholesterol occlusion is the proximate cause of ischemia and infarction and the specification of those patents are hereby incorporated by reference. The inventor's conception is that cholesterol accumulation in arteries results in loss of surface antithrombotic effects of sufficient Nitric Oxide and Heparin Sulphate which, prevent endothelial and artery based surface thrombotic activity.

It is also a conception of the inventor that a cellular environment (cellular matrix or gel matrix) composed of charged polymers-highly charged peptide-water polymers, such as heparin-arginine-water is responsible for controlling the structure and ultimately the function of human cells within this cellular environment. As the human blood vessel is only one cell thick, it too operates within this charged polymer-highly charged peptide-water environment. Thus, this charged polymer-arginine-water environment impacts such important functions of the cells by effecting protein distribution and functionality, cell signaling processes, genetic or DNA-RNA transcription regulation, and the physical/chemical properties of cells, including blood vessel wall cells. It should also be noted that heparins or heparin domains within these polymer structures are members of the group commonly referred to as endogenous heparans. Exogenous heparans, including heparin, have functions which protect the endogenous heparans.

The present invention is directed to a formulation for treatment of the gel matrix or cellular environment and inhibiting cardiovascular disorder or disease and endothelial dysfunction. In accordance with the invention, a patient susceptible to or suffering from a cardiovascular disorder or disease such as atherosclerosis, arteriosclerosis, congestive heart failure, angina pectoris, or other diseases associated with the cardiovascular system, is treated with a therapeutically effective amount of a substance characterized as Rhamnan Sulphate or its functional analogs or physiologically acceptable salts.

A therapeutically effective amount of Rhamnan Sulphate is defined primarily by clinical response in a patient, and ranges from about 2,000 IU to 200,000 IU equivalent of heparin activity daily on variable schedule.

When absorbed into the charged polymer-highly charged peptide-water matrix, Rhamnan Sulphate protects and reinforces structure and roles of endogenous heparin. Whatever the mechanism, Rhamnan Sulphate absorption has a potent effect on surface antithrombotic effects on the cell surface rather than the plasma anticoagulation.

For example, the Rhamnan Sulphate is characterized such that it should be an amount sufficient to exert cell surface anti-thrombotic effects on the endothelial cells, while not increasing the patient's risk of internal or external hemorrhaging and effectively maintaining integrity and functionality of the cellular membranes and surrounding environments of the endothelial cells.

Again, effective doses of Rhamnan Sulphate vary with the particular patient condition and the method of administration. For example, it is noticed that subcutaneous injection of heparin results in greater concentration in the cellular and membrane domains than intravenous injection, and it is the inventor's observation that oral heparan sulphates localizes almost exclusively to cell surface membranes, especially the endothelium. Thus, the preferred method of administration of Rhamnan Sulphate for the present invention is through the oral route, while the least preferred method is via intravenous injection.

The compound of the present invention is preferably formulated for oral, sublingual, subcutaneous, intravenous, transdermal or rectal administrations in dosages and in admixture with pharmaceutical excipients or vehicles including implantation or controlled-release devices. For example, the compound of Rhamnan Sulphate can be dispersed in a physiologically acceptable, non-toxic liquid vehicle, such as water.

Furthermore, the compound of the present invention is optionally used, either alone or in conjunction with other material that are currently used as capsules, to form a capsule shell. The capsule shell comprised of the compound of the present invention is then used to administer or deliver other pharmaceuticals, nutrients, or vitamins and minerals.

Alternatively, the compound can be given in tablet, capsule, powder, granules or coated tablet form. The compound is made using conventional methods, and may be mixed with conventional pharmaceutical auxiliaries, such as binders, fillers, preservatives, tablet disintegrators, flow regulators, plasticizers, wetting agents, dispersants, emulsifiers, solvents, retarding agents and/or anti-oxidants. It is also optionally contained or formed into a complex with lipids in various formulations and molecular arrangements.

The inventor recognizes as integral to the invention, that cell surface based antithrombotic activity is distinctly different from plasma anti-coagulation. The invention achieves cell based antithrombotic activity without the inhibition of plasma anticoagulant factors. Thus, the invention avoids the risks of spontaneous hemorrhage or excessive bleeding due to vessel injury attendant to plasma anticoagulation with currently available anticoagulant treatments such as Coumadin® and heparin.

Localization of administered heparin or heparin analogues to cell surfaces (e.g. endothelial surfaces) by oral administration inhibits thrombotic activity within and on artery and blood vessel surfaces without the inhibition of plasma clotting factors seen with currently available anticoagulants.

An efficiently operating homeostatic system is crucial to cellular function within mammalian organisms. In a healthy state, there is formed a gel matrix of heparin, highly charged peptide and water polymers, which houses a plurality of other molecules by accommodating dynamic binding of and release of such molecules without reaching concentration levels which destroy the gel structure and its regulatory functionalities.

Rhamnan Sulphate is derived from plant sources such as algae. Typical plant sources of Rhamnan Sulphate and Rhamnan Sulphate analogs includes, Monostroma Nitidum.

Such plants are considered to be an effective and efficient source of Rhamnan Sulphate compounds for use in the present invention.

Long chain charged polymer strands are an organizing determinant for membranes, proteins, receptors, ion channels, cell organelles, nuclear membranes, membrane pores, and other complex cellular constituents. The polymers and highly charged amino acids such as Arginine organize water into arenas for confining bilipid layer membranes, for example, creating cell turgor and form and limiting hydrolytic properties of water on other molecular structures.

Rhamnan Sulphate's high sulphate content imparts a high negative charge which attracts and binds positively charged substances like basic amino acids, basic domains of proteins and peptides, cations, water and other such charged molecules. Arginine has a high positive charge and strongly associates with heparin along membrane surfaces such as endothelium and basement membranes an in association with water, organize as gel matrix.

The gel may be in a constant state of change, including transitions from one state or phase to another. As such, conformation can change and derangements occur as different substances move in and out of the gel and as the gel properties change.

A healthy gel matrix is formed from endogenous charged polymers, endogenous arginine and water. An unhealthy state of a gel matrix has some of the highly charged peptides molecules cleaved out of the gel. Likewise, charged polymers have been removed from the gel. There are thus created gaps between charged polymers into which other molecules can embed or pass through.

The healthy gel structure has a conformation that preferentially supports interaction and binding of foreign molecules. The capacity to accommodate intrusions of such molecules before the gel structure collapses and loses its functionality is an important characteristic of the gel system.

An example of polar molecules that heparin binds and inactivates, thereby modulating their activity, are serine proteases, other clotting factors and thrombolytic agents, antithrombin-thrombin, complement, apo-lipoproteins, growth-promoting factors, mitogens, heparinase, lipoprotein lipase, growth-inhibiting factors, chemotactic factors, super oxide dismutase, cytokines, numerous enzymes, and cytoskeletal proteins such as fibronectin.

As these intrusions accumulate locally or in a distributed fashion, they cause an interference within the gellular association of charged polymers and highly charged peptide. The interference can cause the gel structure to deteriorate, thus increasing its porosity or collapse altogether in a localized or distributed fashion. In addition, the intrusion may trigger a release of other bound polar molecules, such as calcium, which would induce a non-homeostatic event.

The permeability created by the interference of such molecules allows macromolecules or cells to enter and traverse the gel. For example, cholesterol, clotting factors and water traverse the gel reaching a bilipid layer, or other subendothelial locations. In addition, ionic strength, flow stress, heat, osmotic pressure or other forms of energy transfer to the gel can deteriorate the properties of the gel as described above.

These intrusions result in a displacement of arginine and decreased generation of nitric oxide as an additional effect. Intrusions limit the binding capacity of the heparin for arginine and other molecules within the gel.

In order to reverse this disruption of the gel matrix caused by the removal of arginine and/or heparin, the present invention employs Rhamnan Sulphate to maintain and rejuvenate the gel matrix and its functionality. In this regard, the present invention utilizes Rhamnan Sulphate to give optimal pore closure and stabilization, and number and distribution of binding sites, wherein signaling, anti-proliferation, cell surface anti-thrombotic, and anti-inflammatory effects are maintained. Thus, the homeostasis-promoting functionalities of heparin, arginine, and charged polymer-highly charged peptide-water gel matrix, resultant from the hereindescribed composition, retard continuous and accumulative change and injury to cellular domains. By this retarding effect, cholesterol accumulations, generally referred to as "arterial plaques" are minimized.

Administration of Rhamnan Sulphate also leads to increased lipoprotein and lipase release and tissue factor pathway inhibitor release, with beneficial effects on plaque stability, growth, rupture, and regression.

Addition of Rhamnan Sulphate to the gel system protects the functionality of both heparin and the arginine in the gel matrix. In the extragellular medium, the ability of heparin to bind and quiesce molecules is augmented by simultaneous addition of Rhamnan Sulphate, wherein Rhamnan Sulphate binds to extragellular potentially-intruding molecules, thus allowing existing gellular charged polymers to associate with gellular arginine.

Nitric oxide produced from arginine is an important physiological mediator. The enzyme responsible for nitric oxide production, nitric oxide synthase, requires CA++ and Calmodulin. The functionality of the heparin-arginine gel includes its binding and regulation of CA++ and Calmodulin. By regulating Calmodulin activity, the effects of Rhamnan Sulphate on the charged polymer-arginine gel regulates nitric oxide synthase activity responsible for nitric oxide production.

The binding of water, small anions and cations within the charged polymer-arginine-water gel is facilitated by pi-bonding properties inherent in the saccharide ring structure within the charged polymers. Changes in the shared electron density and electrical charge variation regulated the state of solvation and conformation of the gel polymers. Thus, small anion and cation binding induces changes in the state of solvation, changes in catalytic and hydrolytic properties of water, and changes in capacity of the gel to bind water and other molecules. Low to high molecular weight Rhamnan Sulphate, preferably having a high degree of sulfation, is preferably used.

Endothelial cell injury and myocardial cell injury occur from free radicals. Heparin binds super oxide dismutase which absorbs high energy electrons and deactivates free radicals. Rhamnan Sulphate, heparin and nitric oxide bind free radicals preventing damages to endothelial cells.

Congestive heart failure is in part due to free radical injury to myocardial cells. Rhamnan Sulphate, heparin, super oxide dismutase and nitric oxide all attack and neutralize free radicals, therefore, diseases associated with cellular injury from free radicals are effectively treated and prevented by the present invention. Also, Rhamnan Sulphate aids in the reconstruction of damaged tissue by promoting the production of endogenous heparin, which then forms a complex with and removes extracellular matrix protein accumulations, e.g. fibronectin with consequent reversal or minimization of organ hypertrophy states. Rhamnan Sulphate enhances regeneration of endothelium following an injury to an endothelium surface.

EXAMPLE 1

Dried green Algae (Monostroma Nitidum) was swollen in 10 Vols. Of water at room temperature for one hour. Thereafter the swollen green algae was ground and refluxed for two (2) hours in a boiling water bath. The water extract was centrifuged (4500 g) for 30 minutes, and the water-soluble polysaccharide in the non-dialyzable fraction was obtained by lyophilization.

The crude polysaccharide was dissolved in water and was applied to a column (2.4×100 cm) of DEAE-cellulose (Whatman DE-52). Starch or neutral polysaccharides were removed by continuous water elution until the sample was completely free as determined by phenol-sulfuric acid detection. Afterwards, acid polysaccharide was fractionated by stepwise alteration of the ionic strength of KCL at 0.5. 0.7 and 2.0 M, and then each fraction was desalted and freeze dried. The 0.5 M KCL fraction (major fraction) successive purification procedures were performed by gel filtration chromatography on a Toyopearl HW-65 (fine) column (1.2× 100 cm). The sample was eluted with water at a flow rate of 0.4 ml/min. The major fraction was collected and freeze dried. These procedures or variations of them for extraction of Rhamnan Sulphate is well known.

EXAMPLE 2

Rhamnan Sulphate was prepared as described in Example 1 and was tested for cell surface anti-thrombotic activity, as described below. Rhamnan sulphate was dissolved in water at concentrations 20, 10 and 5 mg/ml. For experiments utilizing L-Arginine, L-Arginine capsules were opened and contents were dissolved in water at 300 mg/ml for 4 hr studies and 150 mg/ml for the 28 day study. Rhamnan sulphate-arginine complex (RS–LR), where L-Arginine is covalently bound to Rhamnan Sulphate to form a physiologically acceptable salt of Rhamnan Sulphate, was dissolved in water at concentrations of 20, 10, 3 and 0.3 mg/ml. Bovine ung unfractionated heparin, 150 units/mg, Lot No ZX320, was obtained from Upjohn Ltd. Heparin was dissolved in water at a concentration of 20 mg/ml.

One hundred and two male Wistar rats, weighing 312±64 g (±SD), were handled and housed according to the Principles of Animal Care set out by the Canadian Federation of Biological Societies. The animals were fasted overnight prior to treatment and were anaesthetized with barbital and methoxyflurane for experimental procedures.

Rhamnan sulphate was administered to rats at 7.5, 4 and 2 mg/kg with 5, 20, and 5 rats/group respectively. Rhamnan sulphate (7.5 mg/kg) plus arginine (112.5 mg/kg) was administered to 5 rats. Rhamnan sulphate-arginine complex was administered to rats at 4, 1 and 0.1 mg/kg with 20 rats/group. The rhamnan-arginine complex was weighed fresh daily. All of the Groups and the administered compounds are shown in Table 1. Six to 8 rats were treated per day. A stomach tube was filled with 0.2 ml saline followed by 0.09–0.18 ml of the rhamnan sulphate solutions or 0.1 ml of arginine solution depending on rat weight. Thus when the stomach tube was placed in the stomach the drugs were first introduced into the stomach followed by saline to give a total volume of approximately 0.4 ml. In the heparin alone group, heparin was administered in a volume of 0.1–0.2 ml followed by 0.2 ml saline. Control group was saline alone.

TABLE 1

| | |
|---|---|
| Group 1 | No Treatment |
| Group 2 | Heparin alone at 7.5 mg/kg |
| Group 3 | Rhamnan Sulphate alone at 7.5 mg/kg |
| Group 4 | Rhamnan Sulphate alone at 4 mg/kg |
| Group 5 | Rhamnan Sulphate alone at 2 mg/kg |
| Group 6 | Rhamnan Sulphate 7.5 mg/kg + L-Arginine 112 mg/Kg |
| Group 7 | Salt of Rhamnan Sulphate 4 mg/kg – L-Arginine |
| Group 8 | Salt of Rhamnan Sulphate 1 mg/kg – L-Arginine |
| Group 9 | Salt of Rhamnan Sulphate 0.1 mg/kg – L-Arginine |

Thrombosis Test

The thrombosis test was performed by a modification of the procedure by Blake et al. For animals exposed to treatment for 4 h, a thrombus was initiated in the right jugular vein by application of 10% formalin in 65% methanol to the exposed adventitial surface. Immediately following, drugs were introduced into the stomach by stomach tube. At 4 h after thrombus initiation animals were again deeply anaesthetized and first examined for any external signs of bleeding. The jugular vein was exposed and examined for the presence of a plug using a cotton pledget. The clot was scored as + (hard clot) if the vessel is blocked and remained blocked despite examination with a cotton pledget. The clot was scored as +/–(soft clot) if the vessel appeared completely blocked on first examination and then opened as it was examined. The thrombus was scored as – (negative) if blood was seen to flow freely in the vessel.

Collection of Blood and Blood Vessels

Immediately after examination of the jugular vein, a laparotomy was performed and a blood sample of approximately 10 ml (9 parts blood to 1 part 3.8% sodium citrate) was taken from the abdominal aorta. Plasma was prepared. As a source of endothelium, the thoracic aorta or vena cava was removed and placed in saline. Each animal was examined for signs of internal hemorrhage and the time when blood clotted in the body cavity was recorded.

Harvesting of Endothelium

Endothelium was removed from blood vessels according to the method of Hiebert and Jaques. The vessels were slit open, pinned to dental wax lumen side up, and rinsed in Locke's solution. Cellulose acetate paper was applied to the lumenal surface and when lifted, endothelium was removed. The length and width of the imprint were measured to the nearest mm.

Determination of Heparin-Like Compounds with Endothelium

Cellulose acetate paper was removed from endothelium by dissolving in cold acetone followed by centrifuging and discarding the supernatant. The precipitates were further processed by digestion with pronase (10 µl of 40 mg/ml in Tris buffer). Samples were then centrifuged at 10,000 rpm for 10 min, supernatant was collected and the precipitate washed twice with 100 uL 26.8% NaCl which was added to the supernatant. Glycosaminoalycans ("GAGs") were precipitated from the supernatant with five volumes of methanol and the precipitate dried. Agarose gel electrophoresis was used to identify and measure rhamnan sulphate in endothelial extracts by previously published methods. The dried powders, dissolved in suitable volumes of water, were applied to agarose gel slides along with the administered rhamnan sulphate used as a reference. Following electrophoresis, gels were fixed in 0.1% hexadecyltrimethylammonium bromide and air dried. Slides were stained with 0.04% toluidine blue in 80% acetone and background color was removed with 1% acetic acid. Heparin was identified by electrophoretic migration as compared to reference material and amounts determined by densitometry.

Statistical Analysis

Thrombosis data is expressed as a percentage with 95% confidence intervals. $X^2$ test for differences between proportions was used to compare the total thrombotic incidence and incidence of hard clots between groups. Other data is expressed as mean±SE. A one-way ANOVA with Tukeys post hoc test was used to compare the differences between groups when plasma coagulation tests and heparin-like concentrations in urine were examined.

Thrombosis Test

As shown in FIG. 1 an antithrombotic effect was observed with all oral doses of rhamnan sulphate alone, except 2 mg/kg. As well an antithrombotic effect was seen when arginine was added along with rhamnan sulphate or when rhamnan sulphate was complexed to arginine. At 2 mg/kg rhamnan sulphate there was a trend towards a significant reduction in hard clots versus controls although this did not reach significance. A dose response was evident with both rhamnan sulphate alone or when rhamnan sulphate was complexed to arginine. The rhamnan sulphate arginine complex was a significantly more effective antithrombotic agent than rhamnan sulphate alone as shown by a decrease in incidence of hard clots when comparing the compounds at 4 mg/kg. Further the incidence of hard clots and total thrombotic incidence was less for the rhamnan sulphate arginine complex at 1 mg/kg versus rhamnan sulphate alone at 2 mg/kg.

Figure 2:
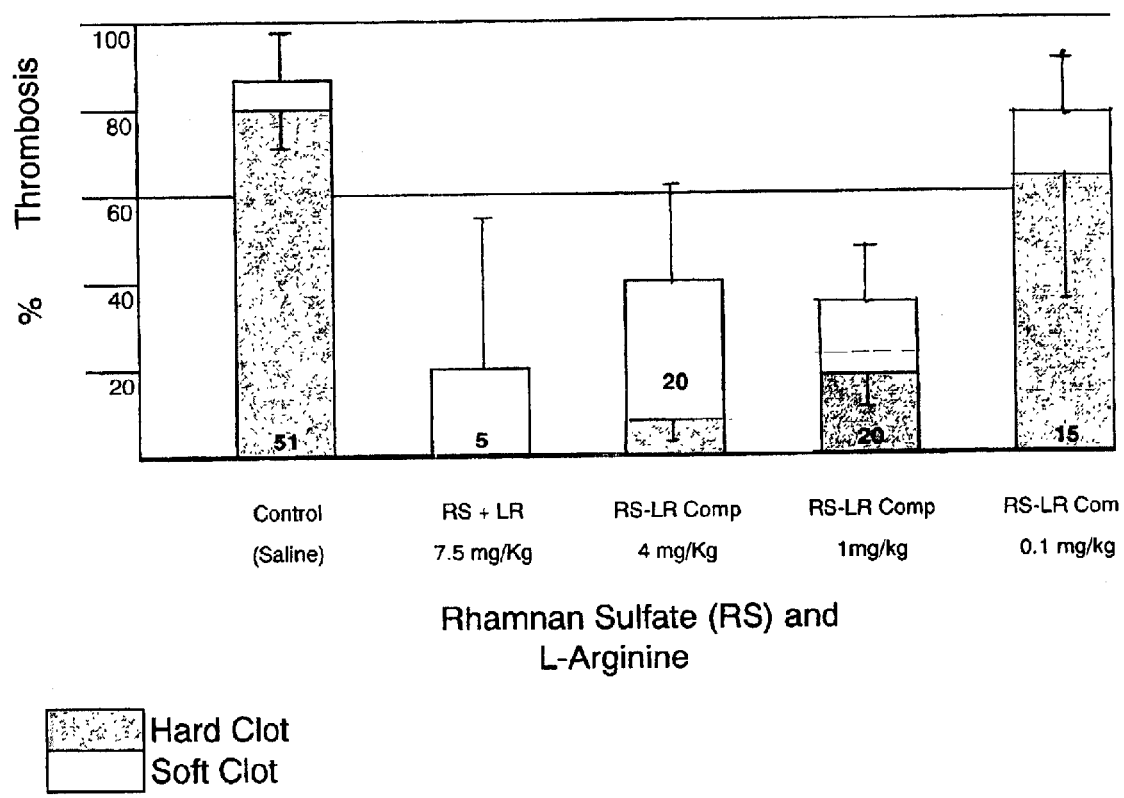
FIG. 2 is a graph comparing a control group to various groups of Rhamnan Sulphate and L-Arginine in various dosages.

FIGS. 1 and 2 show antithrombotic activity of orally administered rhamnan sulphate or rhamnan sulphate and arginine as compared to oral unfractionated heparin. Error bars show 95% confidence intervals; upward bars for total clots, downward for hard clots. RS+LR is 7.5 mg/kg rhamnan sulphate+112.5 mg/kg arginine); RS−LR is 7.5 mg/kg rhamnan sulphate arginine complex. Numbers in bars show number of rats per group.

Plasma Levels

The Rhamnan Sulphate Groups at all doses did not have a significant effect on APTT or the Heptest (Table 2). Rhamnan sulphate alone or when complexed with arginine had little or no effect on anti-Xa or anti-IIa activity. Rhamnan sulphate alone had somewhat more anti-Xa activity than the rhamnan sulphate -arginine complex. When anti-Xa activity was measured in the plasma of rats there was a reduced optical density in the plasma samples from some of the rats given rhamnan sulphate or the rhamnan sulphate-arginine complex. (Data not shown). There was no evidence of bleeding or blood loss in the animals.

TABLE 2

Activation partial thromboplastin time and Heptest following oral administration of rhamnan sulphate alone, with arginine or as a rhamnan sulphate-arginine complex.

|  | Dose mg/kg | APTT (sec) Mean | SE | Heptest (sec) Mean | SE |
|---|---|---|---|---|---|
|  | Controls | 19.5 | 0.9 | 36.3 | 0.8 |
| Rhamnan Sulphate | 7.5 | 20.2 | 0.6 | 32.5 | 2.2 |
|  | 4 | 20.5 | 0.5 | 34.2 | 1.9 |
|  | 2 | 21.8 | 0.9 | 36.5 | 1.1 |
| Rhamnan sulphate + LR | 7.5 | 20.4 | 0.8 | 31.8 | 0.9 |
| Rhamnan Sulphate-Arginine Complex | 4 | 22.6 | 1.5 | 36.9 | 1.0 |
|  | 1 | 18.5 | 0.7 | 30.8 | 0.7 |
|  | 0.1 | 18.5 | 0.7 | 30.8 | 1.0 |

Rhamnan sulphate like material was also found on both aortic and vena caval endothelium. A higher concentration was found on the vena cava than on the aorta when all compounds were administered (Table 3) P<0.00003 one-tailed t-test. A dose effect was evident when venal caval concentrations of rhamnan sulphate were observed following rhamnan sulphate or rhamnan sulphate-arginine. A similar dose effect was seen for aortic concentrations of rhamnan sulphate following oral administration of rhamnan sulphate arginine but not rhamnan sulphate alone. Vena caval but not aortic concentrations were greater at 4 mg/kg for rhamnan sulphate but not rhamnan sulphate-arginine complex.

TABLE 3

Rhamnan sulphate - like material found on aortic and vena caval endothelium following oral administration of rhamnan sulphate alone, with arginine or as a rhamnan sulphate-arginine complex.

|  | Dose mg/kg | Number | Aorta $\mu g/cm^2$ mean ± se | Vena Cava $\mu g/cm^2$ mean ± se |
|---|---|---|---|---|
| Rhamnan Sulphate | 7.5 | 5 | 1.80 ± 0.79 | 11.22 ± 3.20 |
|  | 4 | 20 | 2.05 ± 0.08 | 15.97 ± 1.54* |
|  | 2 | 5 | 2.32 ± 0.33 | 3.00 ± 0.43 |
| Rhamnan sulphate + LR | 7.5 | 5 | 3.91 ± 0.65 | 7.16 ± 3.77 |
| Rhamnan Sulphate-Arginine Complex | 4 | 20 | 2.30 ± 0.07 | 4.41 ± 0.05 |
|  | 1 | 20 | 0.12 ± 0.05 | 0.42 ± 0.10 |
|  | 0.1 | 20 | 0.52 ± 0.13 | 1.89 ± 0.43 |

Rhamnan sulphate-like material was also recovered from the urine and feces accumulated over the 4 hr period. The amounts and concentrations recovered after administration of rhamnan sulphate alone resulted in more being excreted in the urine than when given as a rhamnan sulphate-arginine complex. Amounts recovered were 3.0±0.4 and 1.6±0.4 (mean±SE) percent of dose for rhamnan sulphate alone versus rhamnan sulphate-arginine respectively.

Amounts recovered from feces also show that more is recovered when administered as rhamnan sulphate alone versus rhamnan sulphate-arginine. A dose effect was evident. Amounts recovered were 13.7±4.4 and 6.1±1.9 (mean±SE) percent of dose for rhamnan sulphate alone versus rhamnan sulphate-arginine respectively, these differences were not significant.

In general, the results indicate that Rhamnan Sulphate provides vessel surface anti-thrombotic activity without appreciably increasing plasma anticoagulation activity. Hard clots and soft clots build from the inside surface of the lumen of the injured vessel and extend radially more central into the lumen of the vessel, but there is little or no change in the plasma coagulation activity as was measured by the standard plasma coagulation tests mentioned above. Thus, Rhamnan Sulphate is effective in preventing clot formation at the inside surface of the vessel, but it does not provide the patient with increased plasma anti-coagulation activity to render the patient a "bleeder" or to be at appreciably increased risk of hemorrhaging.

The results show that without any treatment, as a control group, saline had no effect on thrombosis with approximately a 90% incidence of thrombosis of which a very high percentage were hard clots. Heparin, which is commonly used as an anticoagulant, at 7.5 mg/kg showed little or no effect in total incidence of thrombosis, however it reduced the percentage of incidence of hard clots. Conversely, Rhamnan Sulphate at the same 7.5 mg/kg dosage showed a significant decrease in incidence of thrombosis with little or no hard clots. Reduction of the dosage of Rhamnan Sulphate to 4 mg/kg and 2 mg/kg resulted in the increase in incidence of thrombosis and in the re-appearance of hard clots from the 7.5 mg/kg dose.

Figure 3:
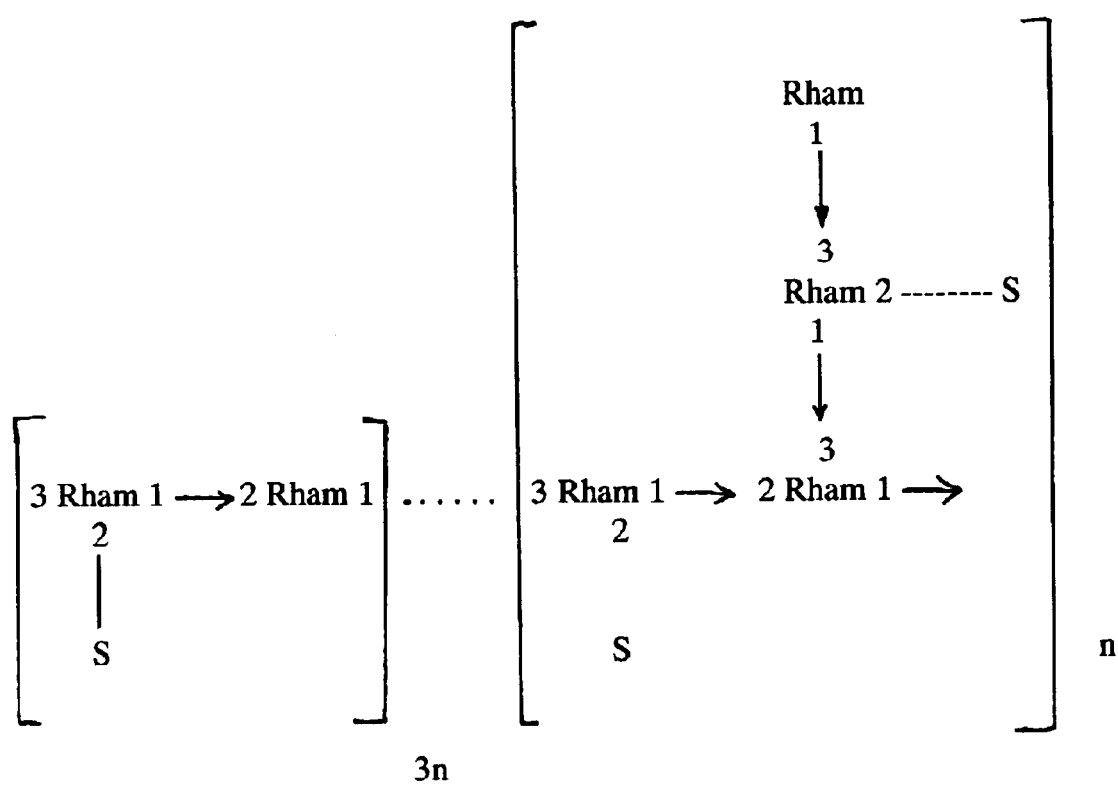
FIG. 3 is a chemical representation of Rhamnan Sulphate.

FIG. 2 again compares the control group with the co-administration of Rhamnan Sulphate with L-Arginine, the structure of which is commonly known. RS+LR refers to the co-administration of Rhamnan Sulphate, whereas RS–LR refers to the salt of Rhamnan Sulphate with arginine as a compound, the chemical structure of which is shown in FIG. 3. Group 6, RS+LR at 7.5 mg/kg, showed little difference with administration of Rhamnan Sulphate by itself both in the incidence of thrombosis and in the non-occurring of hard clots. Group 7, RS–LR compound at 4 mg/kg, however, showed a significant reduction in the total incidence of thrombosis from 4 mg/kg of Rhamnan Sulphate alone and a reduction in hard clots. Even Group 8, LS–LR compound at 1 mg/kg showed a slight decrease in incidence of thrombosis than and hard clots than 4 mg/kg of Rhamnan Sulphate.

The result is that Rhamnan Sulphate by itself is more effective than Heparin in lowering the incidence of thrombosis and in reducing the number of hard clots. Further, that the blood anticoagulation activity is not appreciably increased. This further desired effect is opposite that of Heparin, which is known to increase plasma anticoagulation activity. Thus, the use of Rhamnan Sulphate in treatment of endothelial dysfunction, particularly cardiovascular disease, and more particularly atheresclerosis and arteriosclerosis is desired. A second result is that the salt of Rhamnan Sulphate-arginine compound is more effective in lowering the incidence of thrombosis and hard clots than an equivalent dose of Rhamnan Sulphate alone.

It is therefore evident how the objective of the present invention is satisfied. First the method and composition of the invention possesses extremely potent antithrombotic activity and other inhibitory effects on cell surface coagulation assembly and activity for thrombus inhibition.

Second, since Rhamnan Sulphate is from plant cells, it has no potential for the transmission of potentially lethal and serious prion diseases such as mad cow disease.

Third, Rhamnan Sulphate has no potential for activating Platelet Factor IV and resulting in immune complex destruction of platelets as seen with heparin administration.

Fourth, Rhamnan Sulphate is a functional substitute for heparin in applications requiring systemic (not Plasma) anticoagulant activity such as dialysis, bypass surgery, and polymer tube coatings and devices for use in mammals and humans.

Fifth, the described composition has less peptide residues because it is extracted from plant cells as compared to heparin from animal cells. Hence, it is less allergic reaction prone and has fewer immunogenic properties.

It will be readily apparent to those skilled in the art that many modifications, derivations and improvements are within the scope of the invention. Such modifications, derivations, and improvements should be accorded full scope of protection by the claims appended hereto.

The following is claimed:

1. A method for treatment of the mammalian cellular environment for the treatment of endothelial dysfunction comprising the step of administering to a patient need thereof an amount of Rhamnan Sulphate, or its physiologically acceptable salts, in therapeutic effective amounts.

2. The method of claim 1 wherein the anticoagulation activity in the blood plasma of a patient is not appreciably increased.

3. The method of claim 1 wherein the dose of Rhamnan Sulphate is equivalent to between approximately 2,000 IU and 200,000 IU of heparin activity on a daily basis.

4. The method of claim 1 wherein the dose of Rhamnan Sulphate is equivalent to between approximately 5,000 IU and 20,000 IU of heparin activity on a daily basis.

5. The method of claim 1 wherein the dose of Rhamnan Sulphate is equivalent to between approximately 8,000 IU and 12,000 IU of heparin activity on a daily basis.

6. The method of claim 1 wherein the dose of Rhamnan Sulphate is approximately 7.5 mg/kg as a single dose.

7. The method of claim 1 wherein the dose of Rhamnan Sulphate is repeated daily to treat the incidence of thrombosis.

8. The method of claim 1 wherein the dose of Rhamnan Sulphate is repeated daily to treat the incidence of hard clots.

9. The method of claim 1 further comprising the co-administration of L-Arginine.

10. The method of claim 1 wherein the cardiovascular disease is atherosclerosis.

11. The method of claim 1 wherein the cardiovascular disease is arteriosclerosis.

12. A method of inducing cell surface anti-thrombotic activity in endothelial cells comprising the step of administering to a patient in need thereof an amount of Rhamnan Sulphate, or its physiologically acceptable salts, in therapeutic effective amounts.

13. The method of claim 12 wherein anticoagulation activity in the blood plasma of a patient is not appreciably increased.

14. The method of claim 12 wherein the dose of Rhamnan Sulphate is equivalent to between approximately 2,000 IU and 200,000 IU of heparin activity daily.

15. The method of claim 12 wherein the dose of Rhamnan Sulphate is equivalent to between approximately 5,000 IU and 20,000 IU of heparin activity daily.

16. The method of claim 12 wherein the dose of Rhamnan Sulphate is equivalent to between approximately 8,000 IU 2,000 IU of heparin activity daily.

17. The method of claim 12 wherein the dose of Rhamnan Sulphate is repeated daily to treat the incidence of thrombosis.

18. The method of claim 12 wherein the dose of Rhamnan Sulphate is repeated daily to treat the incidence of hard clots.

19. The method of claim 12 further comprising the co-administration of L-Arginine.

20. A composition comprising an amount of Rhamnan Sulphate, or its physiologically acceptable salts, and L-Arginine, in therapeutic effective amounts.

21. The composition of claim 20 wherein the amount of Rhamnan Sulphate is equivalent to between approximately 2,000 IU and 200,000 IU of heparin activity on a daily basis.

22. The composition of claim 20 wherein the amount of Rhamnan Sulphate is equivalent to between approximately 5,000 IU and 20,000 IU of heparin activity on a daily basis.

23. The composition of claim 20 wherein the amount of Rhamnan Sulphate is equivalent to between approximately 8,000 IU and 12,000 IU of heparin activity on a daily basis.

24. The composition of claim 20 wherein the Rhamnan Sulphate and L-Arginine are formed into a Rhamnan Sulphate L-Arginine complex.

25. The composition of claim 20 wherein the Rhamnan Sulfate and L-Arginine are covalently bound together.

* * * * *